(12) United States Patent
Bailey (10) Patent No.: US 7,637,262 B2
(45) Date of Patent: Dec. 29, 2009

(54) ANTI-RETRUSION ORAL APPLIANCE

(76) Inventor: Dennis R. Bailey, 7901 E. Belleview Ave., Ste. 200, Englewood, CO (US) 80111

( * ) Notice: Subject to any disclaimer, the term of this patent is extended or adjusted under 35 U.S.C. 154(b) by 175 days.

(21) Appl. No.: 11/309,031

(22) Filed: Jun. 12, 2006

(65) Prior Publication Data

US 2007/0283967 A1    Dec. 13, 2007

(51) Int. Cl.
*A61F 5/56* (2006.01)
*A61C 5/14* (2006.01)
*A61C 5/00* (2006.01)

(52) U.S. Cl. .................. 128/848; 128/859; 128/860; 128/861; 128/862; 433/6; 433/7; 433/140

(58) Field of Classification Search ............... 128/848, 128/859, 856, 857, 858, 860, 861, 862; 602/902; 433/6, 7, 34, 37, 41, 42, 43, 44, 140
See application file for complete search history.

(56) References Cited

U.S. PATENT DOCUMENTS

| | | | | |
|---|---|---|---|---|
| 5,092,346 | A | | 3/1992 | Hays et al. .................. 128/848 |
| 5,570,704 | A | * | 11/1996 | Buzzard et al. ............. 128/848 |
| 5,868,138 | A | | 2/1999 | Halstrom .................... 128/848 |
| 6,082,363 | A | * | 7/2000 | Washburn .................... 128/859 |
| 6,092,523 | A | | 7/2000 | Belfer ......................... 128/848 |
| 6,109,265 | A | * | 8/2000 | Frantz et al. ................. 128/848 |
| 6,604,527 | B1 | | 8/2003 | Palmisano .................. 128/848 |
| 6,983,752 | B2 | | 1/2006 | Garabadian ................. 128/848 |
| 7,178,529 | B2 | * | 2/2007 | Kownacki .................... 128/848 |

* cited by examiner

*Primary Examiner*—Patricia M Bianco
*Assistant Examiner*—Ophelia Hawthorne
(74) *Attorney, Agent, or Firm*—Kyle W. Rost (57) ABSTRACT

An oral appliance for treating sleep apnea and bruxism is formed of a maxillary tray and a mandibular tray. The maxillary tray carries a maxillary bite pad projecting downwardly toward an opposed mandibular occlusal surface. The mandibular tray carries a mandibular bite pad projecting upwardly toward an opposed maxillary occlusal surface. The maxillary bite pad is posterior to the mandibular bite pad such that upon sufficient relative posterior movement of the mandibular tray, the maxillary bite pad engages the mandibular bite pad and limits posterior movement of the mandibular tray. At least one surface, chosen from the anterior face of the maxillary bite pad and the posterior face of the mandibular bite pad, defines a guide plane disposed at an upward and forward slant. The maxillary bite pad and the mandibular bite pad are engageable at the guide plane for advancing the mandibular tray along the guide plane upon vertical closure between the trays. A smooth pad is disposed over the occlusal surface of at least one of the trays, guarding the occlusal surface from engagement with the opposed bite pad.

25 Claims, 4 Drawing Sheets

ANTI-RETRUSION ORAL APPLIANCE

BACKGROUND OF THE INVENTION

1. Field of the Invention

The invention generally relates to surgery and more specifically to body protecting or restraining devices for patients. The invention is an antisnoring device as well as a therapy for sleep apnea.

2. Description of Related Art

Including information disclosed under 37 CFR 1.97 and 1.98

An estimated twenty million people suffer from both snoring and sleep apnea. A single cause of both conditions is that the lower jaw and tongue fall back during sleep to partially block the airway. A known treatment is to use an oral appliance that repositions the lower jaw to prevent this partial blocking of the airway. This general category of devices is known as oral airway dilator appliances or mandibular repositioners.

When the airway is partially blocked, normal respiration requires and causes an increase in air speed through the airway. The increased air speed at the mouth and throat causes soft tissue of the uvula and soft palate to vibrate. This vibration causes noise that is known as snoring.

Sleep apnea results from a partial-to-complete blockage of the airway. Increased air speed through the airway will cause an increase in dynamic pressure and a corresponding drop in static pressure. The decreased static pressure tends to further draw back the lower jaw and tongue to further block the airway. This blockage can increase to the point of becoming complete, which at least temporarily interrupts breathing. Thus, sleep apnea also is known as obstructive sleep apnea. Typically, the blockage occurs in the area of soft palate or the base of the tongue. Those suffering from this condition can awaken with coughing and gasping as they try to restore normal breathing.

Oral airway dilator appliances help to open the airway by repositioning the lower jaw and tongue. These appliances prevent the jaw and tongue from falling back during sleep. Most oral dilator appliances are custom fabricated of hard plastics to fit to the upper and lower teeth. Such appliances are made in dental laboratories, based upon molds of the patient's teeth. They will have a separate upper and lower component. The two components or trays are joined together or otherwise interact to reposition the lower jaw. The repositioning takes place by a combination of opening the lower jaw and moving forward the lower jaw.

The lower jaw should be allowed to move during sleep to prevent general discomfort and specifically to avoid soreness in the temporomandibular joints. Custom fabricated appliances might employ swivels or hinges to join the upper and lower plates while allowing the lower jaw to move. Custom appliances tend to be costly because they require significant expertise by the dentist and by the laboratory.

An example of a currently available dental appliance is the elastic mandibular advancement (EMA) appliance that is the subject of U.S. Pat. No. 6,109,265 to Frantz et al. According to this patent disclosure, upper and lower trays are releasably joined together by a linear elastic band arranged to pull the jaw forward. Each tray carries a retention hook that engages an end of the elastic band. The upper hook is forward of the lower hook, such that the elastic band pulls the jaw forward when engaged on upper and lower retention hooks. The lower tray also carries a bite plane that opens the bite vertically. A limitation of this device is that because only elastic bands are applied to control front-to-back jaw position, the jaw muscles may suffer hyperactivity during sleep. As a result, the patient may continue to have disrupted sleep and discomfort.

A recently developed appliance for treating sleep disorder is the subject of U.S. Pat. No. 6,983,752 to Garabadian. According to this disclosure, separate upper and lower trays each carry a bite pad for separating the upper and lower jaws. In addition, the lower bite pad is anterior to the upper bite pad, such that the upper bite pad interferes with posterior movement of the lower bite pad to block the lower jaw from retracting. Each tray carries a pair of hooks for engaging an x-shaped elastic band. The elastic bands are adjustable on the hooks for selecting vertical and horizontal forces. Several limitations in the disclosed appliance are notable. The bite pads are relatively short in front-to-back dimension, which can induce the jaw to pivot and lead to muscle hyperactivity. The bite pads engage one another at vertical abutting surfaces that are substantially perpendicular to the front-to-back axis of the mouth, producing an abrupt stop that is likely to further induce muscle hyperactivity. Each bite pad impinges upon an occlusal surface of the opposite tray, which is conformed to the occlusal surface of the covered tooth. The roughness of this interaction interferes with jaw movement and might exacerbate sleep bruxism or clenching.

Another recently developed mandibular advancement device is the subject of U.S. Pat. No. 6,604,527 to Palmisano. The disclosure shows that upper and lower jaws respectively are fitted with upper and lower plates. The upper plate carries a depending side flange in the area near the posterior teeth, and the lower plate carries an upstanding side flange in a similar position. The side flange on the upper plate is posterior to the side flange on the lower plate and positioned to block the lower flange so as to prevent undesirable posterior movement of the lower plate. The positioning of the flanges to the side of the teeth offers several advantages: the lower jaw can close to a greater degree than possible with various other appliances; and the flanges can be vertically long so that the abutting surfaces continue to engage even if the jaw opens by a substantial amount. However, the length of the abutting surfaces can create an additional problem. The extremely long flanges may need to be contoured to the path of jaw movement, which can be complex. Further, locating the flanges to the side of the teeth can impose a limitation on lateral movement between the jaws, which may contribute to sleep bruxism.

Airway dilator appliances of the boil-and-bite variety can be fabricated of softer plastics and may be fitted to the patient in the dentist's office, without requiring the assistance of a laboratory. U.S. Pat. No. 5,868,138 to Halstrom shows an example of a boil-and-bite appliance that provides a swivel between upper and lower plates. Other boil-and-bite appliances provide a dental overlay that is molded to only the upper plate or only the lower plate. A single plate boil-and-bite appliance might employ a guide ramp and external shield. U.S. Pat. No. 5,092,346 Hays et al is an example of an upper plate dental overlay that employs a ramp structure that retains the lower jaw in a forward position. U.S. Pat. No. 6,092,523 to Belfer shows an upper plate dental overlay slidably coupled to a guide ramp that permits the lower jaw to move laterally.

As discussed above, sleep disorders such as sleep apnea and snoring are interrelated and may be found in the same patient. Likewise, the same patient may require treatment for sleep bruxism. Each of these conditions is subject to treatment by use of an oral appliance. Individual appliances for each condition may be impractical, due the frequency of the same patient needing treatment for more than one of these conditions or all of these conditions. Therefore, it would be desirable for a single oral appliance to address the combined needs for alleviating snoring, sleep apnea, and sleep bruxism.

An oral appliance worn during sleep should allow vertical and lateral jaw movement to discourage sleep bruxism. At the same time, an appliance should contribute to stability of the lower jaw to reduce snoring and prevent sleep apnea. It would be desirable to combine these characteristics in a single oral appliance.

To achieve the foregoing and other objects and in accordance with the purpose of the present invention, as embodied and broadly described herein, the method and apparatus of this invention may comprise the following.

BRIEF SUMMARY OF THE INVENTION

According to one aspect of the invention, an oral appliance for treating sleep apnea and bruxism is formed of a maxillary tray and a mandibular tray. The maxillary tray carries a maxillary bite pad projecting downwardly toward an opposed mandibular occlusal surface. The mandibular tray carries a mandibular bite pad projecting upwardly toward an opposed maxillary occlusal surface. The maxillary bite pad is posterior to the mandibular bite pad such that upon sufficient relative posterior movement of the mandibular tray, the maxillary bite pad engages the mandibular bite pad and limits posterior movement of the mandibular tray. At least one surface, chosen from the anterior face of the maxillary bite pad and the posterior face of the mandibular bite pad, defines a guide plane disposed at an upward and forward slant. The maxillary bite pad and the mandibular bite pad are engagable at the guide plane for advancing the mandibular tray along the guide plane upon vertical closure between the trays. A smooth pad is disposed over the occlusal surface of at least one of the trays, guarding the occlusal surface from engagement with the opposed bite pad.

According to another aspect of the invention, an oral appliance for treating snoring, sleep apnea, and sleep bruxism is formed of a maxillary tray and a mandibular tray. The maxillary tray carries a maxillary bite pad projecting downwardly toward an opposed mandibular occlusal surface. The mandibular tray carries a mandibular bite pad projecting upwardly toward an opposed maxillary occlusal surface. The maxillary bite pad is posterior to the mandibular bite pad such that upon sufficient relative posterior movement of the mandibular tray, the maxillary bite pad engages the mandibular bite pad and limits posterior movement of the mandibular tray. At least one surface, chosen from the anterior face of the maxillary bite pad and the posterior face of the mandibular bite pad, defines a guide plane disposed at an upward and forward slant. The maxillary bite pad and the mandibular bite pad are engageable at the guide plane, advancing the mandibular tray along the guide plane upon vertical closure between the trays.

According to a further aspect of the invention, an oral appliance for treating snoring, sleep apnea, and sleep bruxism is formed of a maxillary tray and a mandibular tray. The maxillary tray carries a maxillary bite pad projecting downwardly toward an opposed mandibular occlusal surface. The mandibular tray carries a mandibular bite pad projecting upwardly toward an opposed maxillary occlusal surface. The maxillary bite pad is posterior to the mandibular bite pad such that upon sufficient relative posterior movement of the mandibular tray, the maxillary bite pad engages the mandibular bite pad and limits posterior movement of the mandibular tray. A smooth pad is disposed over the occlusal surface of at least one of said trays, guarding the occlusal surface from engagement with the opposed bite pad.

The accompanying drawings, which are incorporated in and form a part of the specification, illustrate preferred embodiments of the present invention, and together with the description, serve to explain the principles of the invention. In the drawings:

DETAILED DESCRIPTION OF THE INVENTION

With reference to the drawings, the invention is an oral appliance 10 for the treatment of sleep apnea, snoring, and sleep bruxism in a human user in need of such treatment. This appliance is designed to maintain the airway in open condition through vertical repositioning of the lower jaw with advancement as required. The appliance is composed of two parts, an upper component 12 and a lower component 14. Each part is fitted to conform to the user's teeth of the respective upper or lower jaw. An elastic member 16 is applied to each side of the appliance, joining the upper and lower components while permitting the lower jaw to move during sleep.

The appliance 10 is adjusted to this limiting position by locating a pair of the interacting stops or bite pads 28, 30 in the posterior of both the right and left sides of the appliance 10. The upper and lower bite pads are configured to contact one another in such a way that the mandible and tongue are prevented from falling back and collapsing the airway. The mandible and associated structures, such as the tongue and collapsible airway, are supported. The bite pads 28, 30 are configured to interact in a self-guided, non-abrupt manner.

Within this specification, the following conventions will be observed: the user or patient is in anatomical position, standing erect with eyes and head facing forward. Anterior refers to the front of the body or toward the front of the mouth. Posterior refers to the back of the body or toward the back of the mouth. Horizontal refers to disposition in a plane perpendicular to the standard median or coronal plane, conforming to the general concept of horizontal placement relative to standard anatomical position. Vertical refers to disposition in a standard median or coronal plane or any intermediate plane, conforming to the general concept of vertical placement relative to standard anatomical position. Upper or top refers a position relatively above another, with respect to a horizontal plane. Lower or bottom refers to a position relatively below another, with respect to a horizontal plane. Right and left refer to sides of the user or patient in standard anatomical position.

Figure 1:
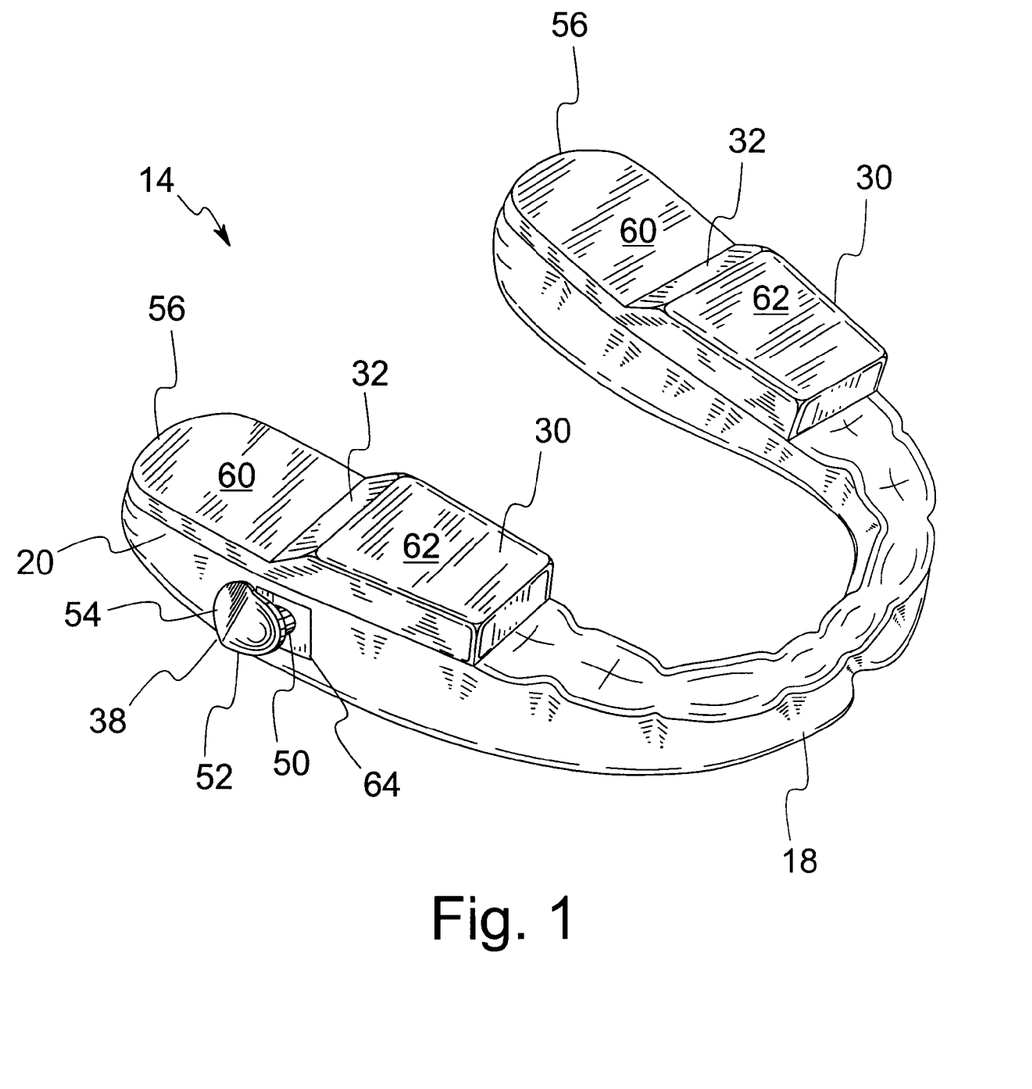
FIG. 1 is an isometric view of a lower jaw component of the oral appliance of the invention.

As best shown in FIG. 1, the lower component 14 is a dental overlay or lower tray conformed to the lower teeth, also known as the mandibular teeth. This tray 14 is formed of thermoplastic material. According to a suitable method of forming, a sheet of thermoplastic material is exposed to elevated temperature sufficient to cause the sheet to become soft. While soft, the sheet is conformed to the shape of a user's teeth. The conformed sheet is then trimmed to remove excess material, producing a shell 18 that is modeled after the user's teeth and fits closely over the teeth.

According to a suitable method of fitting the shell 18, while warm or hot the shell 18 is applied to the user's teeth or to a cast model of the teeth. The shell 18 can be of the boil-and-bite variety, wherein the shell is pre-formed to the approximate configuration of the mandibular teeth so that, at point-of-use, the shell is applied directly to the teeth.

Where direct application is used, the user bites on the warm shell, causing the shell to acquire the impression and general shape of the user's mandibular teeth. A boil-and-bite shell may be lined, either fully or only at selected portions such as at posterior areas 20, with soft plastic filler that is especially suited to conform to and surround the teeth during the fitting process. The shell 18 and filler are allowed to cool to ambient temperature while remaining on the user's teeth. The cooled shell and filler retain the acquired shape. In order to refine the fit, the shaped shell 18 can be further modified, such as by trimming or grinding. The finished fit of shell 18 on the mandibular teeth provides sufficient retention for the shell to be useful in positioning the lower jaw as subsequently described. Additional components are bonded to the shell, as more fully described, below.

Figure 2:
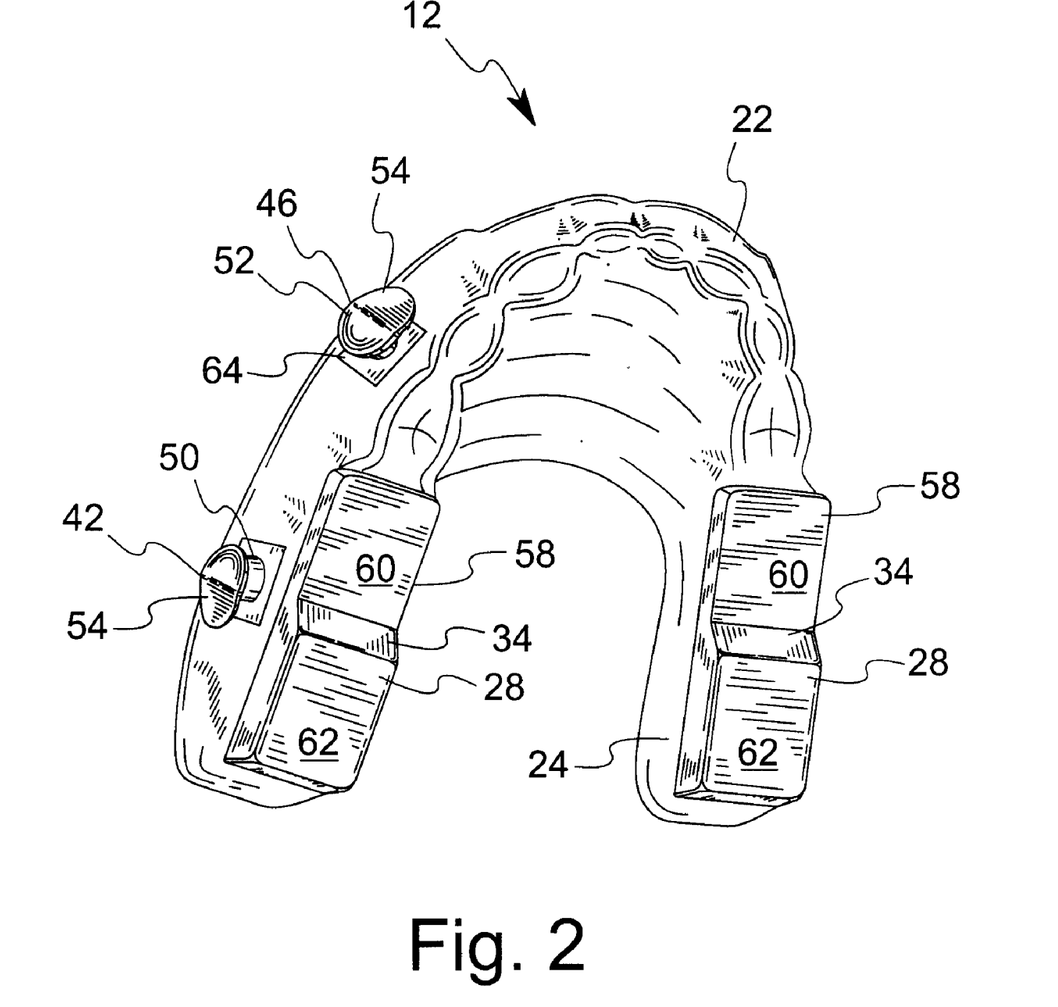
FIG. 2 is an isometric view of an upper jaw component of the oral appliance of the invention.

FIG. 2 shows the corresponding upper component 12, which is a dental overlay or upper tray conformed to the upper or maxillary teeth. Like the lower tray 14, the upper tray 12 is formed of thermoplastic material that is molded to closely fit the patient's teeth. The molded tray is trimmed to produce a closely fitting plastic shell 22. A patient's maxillary teeth are fitted with the upper tray 12 as previously described: either the tray 12 is conformed to a cast model of the user's teeth, or the tray is of the boil-and-bite variety and, while warm, is directly applied to the maxillary teeth. Selected areas such as posterior portions 24 of shell 22 may carry soft plastic filler as previously described. The tray 12 is fitted to the user's upper or maxillary teeth, and the fit may be refined as described, above, or by other established procedures. The finished fit of shell 22 on the maxillary teeth provides sufficient retention for the tray 12 to be useful in cooperating with shell 18 in positioning the lower jaw as subsequently described. Additional components are bonded to the tray 12, as more fully described, below.

Figure 3:
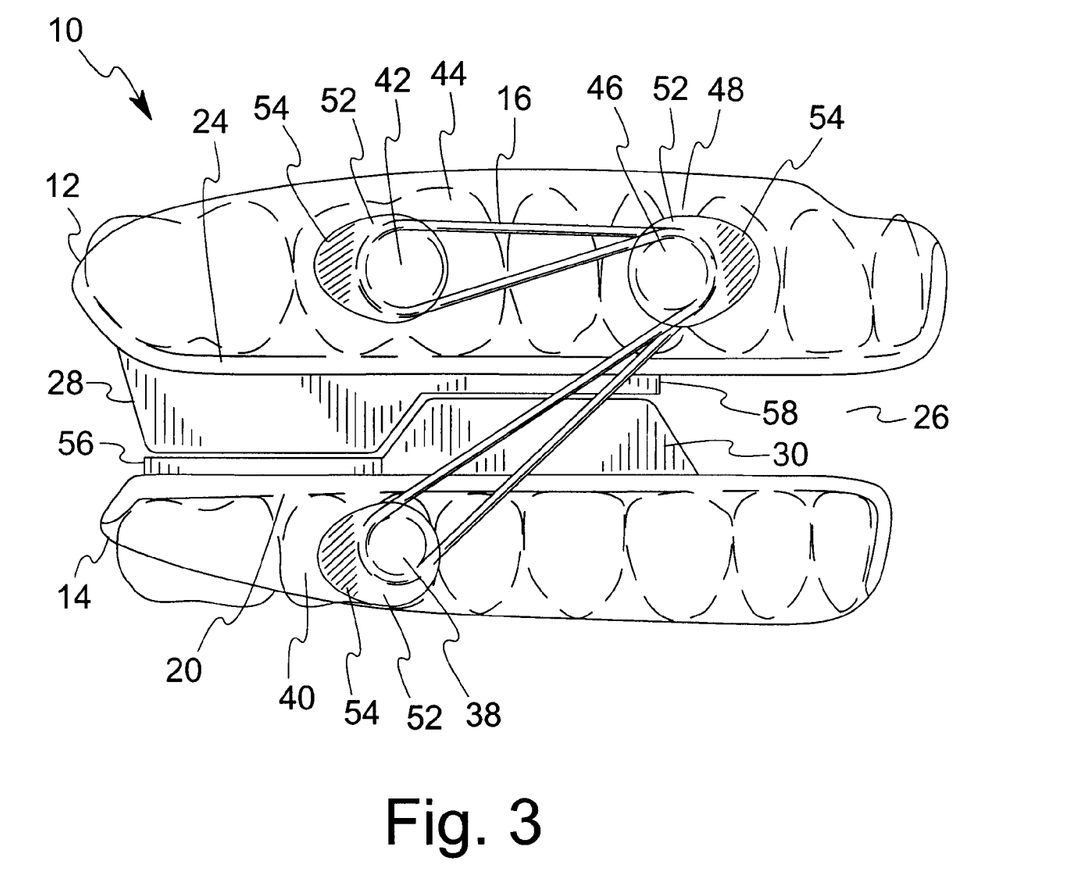
FIG. 3 is a right side elevational view of the oral appliance, showing the upper and lower components in assembled arrangement.

When a human jaw is at rest and not clenched, the upper and lower jaw typically is open by an interocclusal space, best illustrated in FIG. 3. This space provides a suitable position for placement of upper stops or maxillary bite pads 28 and lower stops or mandibular bite pads 30 for the purpose of limiting the posterior movement of the mandible during sleep. Each bite pad extends from an occlusal surface of the corresponding tray. A dentist typically will be consulted to determine an optimum position for the mandible to maintain airway dilation. The dentist can modify the upper tray 12, the lower tray 14, or both trays as required to establish the optimum position to which the mandible should be allowed to retrude during sleep.

The appliance 10 is adjusted to this limiting position by locating a pair of the interacting stops or bite pads 28, 30 in the posterior of both the right and left sides of the appliance 10. The upper and lower bite pads are configured to contact one another in such a way that the mandible and tongue are prevented from falling back and collapsing the airway. The mandible and associated structures, such as the tongue and collapsible airway, are supported. The bite pads 28, 30 are configured to interact in a self-guided, non-abrupt manner.

FIG. 3 shows a relative positioning of the upper and lower trays aligned in a typical jaw position. This alignment allows explanation of the typical relative position of the bite pads. As best shown in FIGS. 2 and 3, maxillary bite pads 28 are relatively nearer the posterior end of the upper tray 12. FIGS. 1 and 3 show that mandibular bite pads 30 are located at a relatively more anterior position on lower tray 14. Due to this relative positioning, upper and lower bite pads on each side of the oral appliance 10 form cooperating pairs. In each pair, the upper bite pad interferes with any bypassing posterior movement of the lower bite pad. In particular, the leading or anterior face 34 of the upper bite pad and the trailing or posterior face 32 of the lower bite pad are opposed contact faces that meet to prevent bypassing posterior movement of the lower bite pad.

An end face of at least one bite pad of each pair is configured as a guide surface or guide plane that is suitably positioned to slidingly engage against the opposed end of the other bite pad. The guide plane is disposed at a non-vertical angle with an upward and forward slant. The guide plane may employ an irregular, non-flat, arcuate, concave or convex surface or surface features that nonetheless allow the described sliding engagement. Thus, although the guide surface may be referred to as a guide plane and may be planar in general characteristics, strict conformity with flatness associated with a plane is not required.

Figure 4:
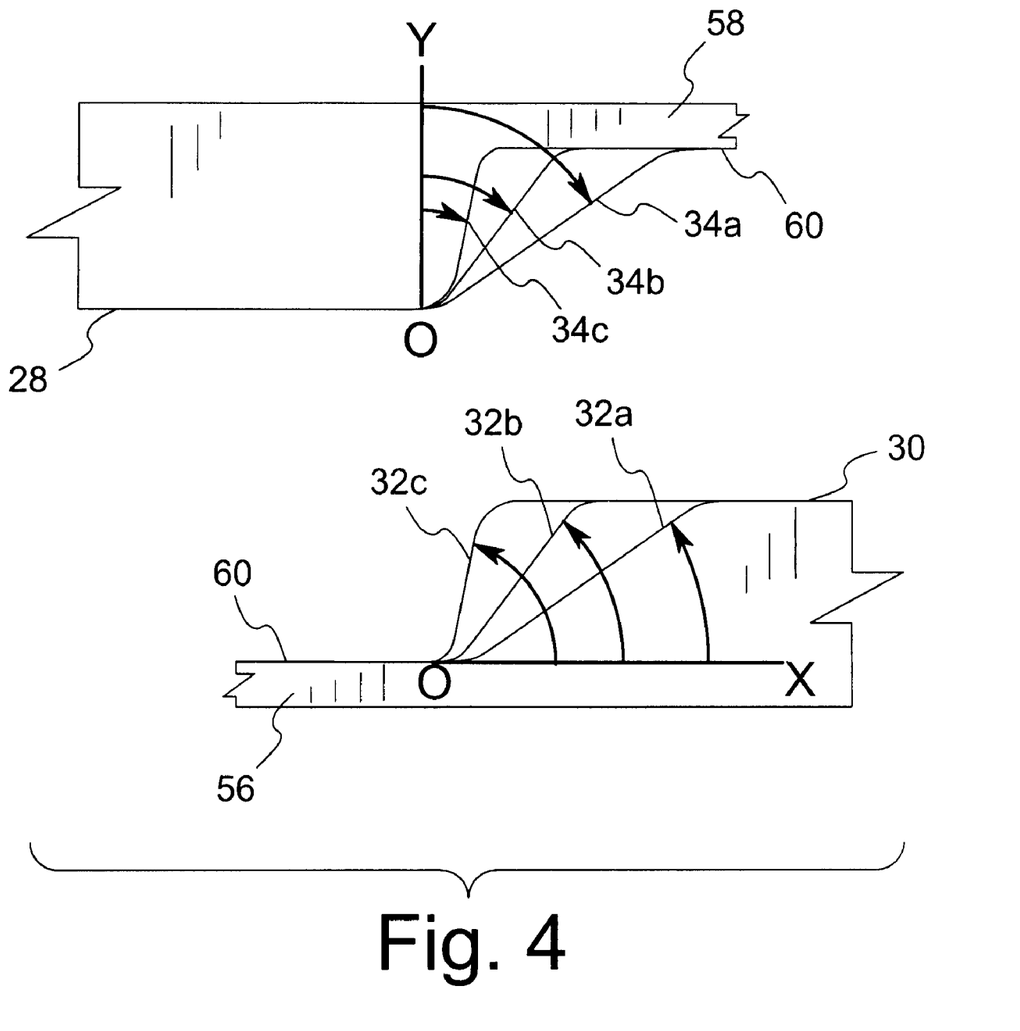
FIG. 4 is a fragmentary view taken from FIG. 3, showing variations of bite planes.

Both bite pads of each pair may have angled opposed surfaces that interact to serve as advancement guide planes for the mandible. Both posterior face 32 of the lower bite pad 30 and the anterior face 34 of the upper bite pad 28 may be angled as guide planes to advance the mandible as the trays vertically close, employing a camming action. The guide planes limit or oppose retrusion of the mandible over their range of engagement as the trays move vertically apart, while continuing to allow free movement of the jaw in other directions.

Where both surfaces 32 and 34 are disposed as guide planes, the guide planes 32, 34 are disposed at non-vertical angles, which may be complementary angles or nearly complementary angles. For example, the faces 32, 34 may reside at complementary angles of forty-five degrees as shown according to the side view of FIG. 3. Guide planes disposed at additional complementary angle pairs are illustrated in FIG. 4 as angle pair 32a, 34a, angle pair 32b, 34b and angle pair 32c, 34c. For clarity, the coordinate axis for the guide planes 32a-c in FIG. 4 is separated from the coordinate axis for guide planes 34a-c.

In measuring complementary angles, the angle of lower tray surface 32 is conventionally measured from an X coordinate of a standard coordinate system, illustrated as axis O-X extending from origin O along coordinate X. Guide plane 32a resides at a relatively low angle of about thirty-five degrees. Guide plane 32b resides at a mid-range angle of about fifty-five degrees. Guide plane 32c resides at a relatively large angle of about eighty degrees. A guide plane 32 may approach the limit of ninety degrees.

The complementary angles of the guide planes of the upper tray surface 34 are conventionally measured from a Y coordinate of a standard coordinate system, illustrated in FIG. 4 as axis O-Y extending from origin O along coordinate Y. Guide plane 34a is disposed at an angle of about fifty-five degrees, which is complementary to the angle of guide plane 32a. Guide plane 34b is disposed at an angle of about thirty-five degrees, which is complementary to the angle of guide plane 32b. Guide plane 34c resides at an angle of about ten degrees, which is complementary to the angle of guide plane 32c.

The use of non-vertical guide planes, especially at complimentary angles in a mid-portion of the range between zero and ninety degrees, is useful to reduce hyperactivity in the jaw during sleep. A middle portion of the range falls between about forty and fifty degrees. The mandible remains capable of movement both forward and back, including movement that would bring the posterior face 32 of bite pad 30 slightly behind anterior face 34 of bite pad 28. Such posterior movement is allowed in conjunction with a necessary opening of the jaw to accommodate the thickness of the bite pads. The movement is guided by the incline of the guide planes at complimentary angles, which avoids abrupt stoppage as can be caused by vertical abutment commonly employed in various prior devices. The incline is sufficient that it self-guides the mandible to return to a more forward position where faces 32, 34 overlie one another as shown in FIG. 3.

Unlike most mandibular repositioning appliances that control the position of the mandible/tongue, this appliance 10 does not rely on attachments located in the anterior, in the tongue space, at the side, in the anterior part of the appliance or in the palate.

While the shape of the guide planes itself provides controlling forces to guide the jaw, additional elastic force can be usefully applied. Side stabilization elastics 16, FIG. 3, provide a gentle horizontal force that urges the lower jaw forward. The elastics 16 may be attached by a Short Class 11 attachment system, which is a three point attachment system that pulls from the mesial aspect. The elastics typically are chosen from 5/16, 3/8, and 1/2 inch elastics to apply from about six to eight ounces of force. This system of elastics provides a gentle, light force, primarily horizontal in nature, that encourages the mandible to maintain an advanced position. The elastics are suitably positioned on the appliance 10 to cooperate with the guide planes 32, 34 to further oppose retrusion of the mandible and the tongue during sleep. Instead of pulling or pushing the mandible forward, this appliance 10 prevents the mandible and tongue from falling back as the musculature relaxes during sleep.

A triangular array of engagement devices supports an elastic 16 in a suitable position on each side of the appliance to cooperate with the guide planes. The lower tray 14 carries a posterior engagement device 38. The preferred front-to-back location for engagement device 38 is near the position of guide plane 32. Relative to the user's teeth, engagement device 38 is located at the mesial buccal cusp of the lower first molar 40, FIG. 3. The upper tray 12 carries a posterior engagement device 42. The preferred front-to-back location of engagement device 42 is near the position of guide plane 34. Relative to the user's teeth, engagement device 42 is located at the mesial buccal cusp of the upper first molar 44. The upper tray 12 also carries a second engagement device, which is the anterior engagement device 46. Relative to the user's teeth, anterior engagement device 46 is located over the embrasure space 48 between the first upper bicuspid and the upper cuspid. The resulting trianglaur arrangement enables application of desirable vector forces in support of the advancement guide planes. In combination with a short class 11 elastic 16, the arrangement provides a gentle force urging forward the mandible.

The elastic 16 is easily applied and securely retained on the engagement devices. In the preferred arrangement of elastic 16 on the three engagement devices, the posterior engagement devices 38, 42 secure the elastic 16 by its end loops. Accordingly, these engagement devices 38, 42 may be regarded as being end hooks and are functionally configured as hooks having a face open to the posterior of the oral appliance 10. Anterior engagement device 46 is offset from the axis between the end hooks and is adapted to engage the middle of elastic 16, directing the span of elastic 16 between hook 38 and engagement 46 at an upward and forward disposition. The anterior engagement device 46 may be regarded as a hook and is functionally configured as a hook having a face open to the anterior of oral appliance 10.

The engagement devices or hooks 38, 42, 46 are configured to easily and reliably receive the elastic 16. Each engagement device provides a post 50 that extends outwardly from a side surface of shell 18, 22. The post carries the elastic. The free or distal end of post 50, relative to the associated shell 18, 22 carries a round or oval cap 52 that is wider than post 50 and retains the elastic from slipping off the distal end of the post. In a preferred configuration of cap 52, a declining portion of the cap extends in the direction of the opening of the hook, as identified above. This extending portion 54 declines toward the associated shell 18, 22. Declining portion 54 serves as an efficient retainer that closes or partially closes the open side of the hook. The elastic is easily applied into the open face of any of the hooks by the method of drawing the elastic into the open face from the round or oval side of the cap 52, which allows the elastic to lift the declining portion 54 as required to enter the open face of the hook.

Forming techniques for a shell 18, 22 cause the occlusal surface of the formed shell to conform to the contours of the underlying teeth, which include many irregularities. In normal use of the oral appliance 10, a bite pad can be expected to frequently contact the occlusal surface of the opposite shell. Particularly when the user is asleep, it would be undesirable for a bite pad to contact an opposite occlusal surface because the irregularities can prevent the jaw from moving. Sleep bruxism may result.

At least one of the bite pads 28, 30 of oral appliance 10, and preferably both, is associated with an adjacent smooth or flat-faced pad that covers and guards the irregular occlusal surface of the shell that otherwise would be subject to contact by the opposed bite pad. Thus, for example, lower bite pad 30 is associated with flat-faced pad 56 that extends posteriorly from bite pad 30. As another example, upper bite pad 28 is associated with flat-faced pad 58 that extends anteriorly from bite pad 28. Each bite pad and its associated flat-faced pad may be formed as a unitary structure in order to establish proper fit and deviations between the flat pad and the bite pad. In another variation, smooth-faced pad 58 may be formed initially as a separate entity, which lies over the occlusal surface of a shell in juxtaposed position to the associated bite pad. In still another variation, smooth-faced pad 58 may be formed initially as a separate entity, which lies over an occlusal surface of a shell and receives the associated bite pad on its outward face.

The smooth-faced pads 56, 58 provide extended, uniform contact faces 60. The bite pads also have a smooth contact face 62. The contact faces are similar in size. When a bite pad contacts an opposed flat pad, the contact faces 60, 62 serve to spread contact pressure over a broad area. There is little resulting tendency for the contact to prevent or overly limit further jaw movement. The bite pad is able slide over the opposite flat pad with little frictional resistance, minimizing any tendency for the oral appliance to induce sleep bruxism.

The oral appliance 10 is custom fitted to each patient. The shell 18, 22 is conformed to the patient's teeth or to a casting of the teeth, as described more fully, above. The flat pad 56, 58 and bite pad 28, 30 are bonded to an appropriate shell in positions suitable to the patient's relative jaw position and tooth locations, typically as determined by a dentist or other professional. The hooks 38, 42, 46 are bonded to the sides of the shells in positions that likewise are suitable to the patient's relative jaw position and tooth locations, as determined by a dentist or other professional. Each hook may have a mounting base 64 that is of larger area than the distal end of the post 50, providing a sufficient area for secure bonding between the post and shell. Bonding may be accomplished using any effective method, such as auto polymerization or light curing.

The resulting oral appliance 10 provides a desirable combination of attributes. Conventional orthodontic elastics (rubber bands) connect the upper and lower trays. The jaw is not held or pulled forward but is prevented from falling back. Posterior support is full length, both upper and lower. The jaw has free movement from side to side and forward. The mouth can open. The palate is open and the tongue has free space. The anterior is open, so patient can lick his lips or drink. The appliance has minimal bulk. Vertical opening is the main mode of action, rather than only mandibular advancement. Finally, the patient is better able to breathe through the nose when the appliance is in place.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. In an oral appliance suited for treating snoring, sleep apnea and sleep bruxism in a patient in need of treatment therefor, formed of a maxillary tray and a mandibular tray, said maxillary tray carrying a maxillary bite pad projecting downwardly toward an opposed mandibular occlusal surface of said mandibular tray, and the mandibular tray carrying a mandibular bite pad projecting upwardly toward an opposed maxillary occlusal surface of the maxillary tray, wherein said maxillary bite pad is posterior to said mandibular bite pad such that upon sufficient relative posterior movement of the mandibular tray, the mandibular bite pad engages the maxillary bite pad and limits posterior movement of the mandibular tray, the improvement comprising:

said maxillary tray and mandibular tray are fitted, in use, to the respective maxillary and mandibular teeth of the patient with sufficient retention to be useful in positioning the patient's jaw;

at least one surface, chosen from the anterior face of the maxillary bite pad and the posterior face of the mandibular bite pad, defines a guide plane disposed at an upward and forward slant;

the maxillary bite pad and the mandibular bite pad are engageable at said guide plane, advancing the mandibular tray along the guide plane upon vertical closure between the trays; and a smooth pad disposed over the occlusal surface of at least one of said trays, guarding said occlusal surface from engagement with the opposed bite pad.

2. The oral appliance of claim 1, wherein both said anterior face of said maxillary bite pad and said posterior face of said mandibular bite pad define guide planes disposed at an upward and forward slant.

3. The oral appliance of claim 2, wherein said guide plane of said maxillary bite pad and said guide plane of said mandibular bite pad are disposed at complementary angles.

4. The oral appliance of claim 3, wherein the complementary angles are equal angles.

5. The oral appliance of claim 3, wherein the complementary angle are between forty and fifty degrees.

6. The oral appliance of claim 1, wherein:

said at least one smooth pad comprises a mandibular smooth pad disposed posterior to said mandibular bite pad and covering said mandibular occlusal surface opposed to said maxillary bite pad, guarding the mandibular occlusal surface from engagement with the maxillary bite pad.

7. The oral appliance of claim 6, wherein said mandibular smooth pad and said mandibular bite pad are formed as a unitary structure.

8. The oral appliance of claim 1, wherein:

said at least one smooth pad comprises a maxillary smooth pad disposed anterior to said maxillary bite pad and covering said maxillary occlusal surface opposed to said mandibular bite pad, guarding the maxillary occlusal surface from engagement with the mandibular bite pad.

9. The oral appliance of claim 8, wherein said maxillary smooth pad and said maxillary bite pad are formed as a unitary structure.

10. The oral appliance of claim 1, further comprising:

a first engagement device carried on the outer side of said maxillary tray in proximity to the anterior end of said maxillary bite pad;

a second engagement device carried on the outer side of the maxillary tray, anterior to said first engagement device;

a third engagement device carried on the outer side of said mandibular tray in proximity to the posterior end of said mandibular tray; and an elastic engaging the first and third engagement devices and extending around said second engagement device, whereby the elastic applies a force urging forward the mandibular tray.

11. The oral appliance of claim 10, wherein each of said engagement devices comprises a post and a cap, said cap is connected to a free end of said post, the opposite end of the post is connected to a respective one of said trays, and one edge of the cap is a declining portion that extends over a side of the post and toward said tray for retaining said elastic;

said declining portion of said first engagement device is disposed toward the posterior of said maxillary tray;

said declining portion of said second engagement device is disposed toward the anterior of the maxillary tray; and said declining portion of said third engagement device is disposed toward the posterior of said mandibular tray.

12. In an oral appliance suited for treating snoring, sleep apnea and sleep bruxism in a patient in need of treatment therefor, formed of a maxillary tray and a mandibular tray, said maxillary tray carrying a maxillary bite pad projecting downwardly toward an opposed mandibular occlusal surface of said mandibular tray, and the mandibular tray carrying a mandibular bite pad projecting upwardly toward an opposed maxillary occlusal surface of the maxillary tray, wherein the said maxillary bite pad is posterior to said mandibular bite pad such that upon sufficient relative posterior movement of the mandibular tray, the maxillary bite pad engages the mandibular bite pad and limits posterior movement of the mandibular tray, the improvement comprising:

said maxillary tray and mandibular tray are fitted, in use, to the respective maxillary and mandibular teeth of the patient with sufficient retention to be useful in positioning the patient's jaw;

at least one surface, chosen from the anterior face of the maxillary bite pad and the posterior face of the mandibular bite pad, defines a guide plane disposed at an upward and forward slant;

whereby, the maxillary bite pad and the mandibular bite pad are engageable at said guide plane, advancing the mandibular tray along the guide plane upon vertical closure between the trays.

13. The oral appliance of claim 12, wherein said guide plane of said maxillary bite pad and said guide plane of said mandibular bite pad are disposed at complementary angles.

14. The oral appliance of claim 13 wherein the complementary angles are equal angles.

15. The oral appliance of claim 13, wherein the complementary angle are between forty and fifty degrees.

16. The oral appliance of claim 12, further comprising:
a first engagement device carried on the outer side of said maxillary tray in proximity to the anterior end of said maxillary bite pad;
a second engagement device carried on the outer side of the maxillary tray, anterior to said first engagement device;
a third engagement device carried on the outer side of said mandibular tray in proximity to the posterior end of said mandibular tray; and
an elastic engaging the first and third engagement devices and extending around said second engagement device, whereby the elastic applies a force urging forward the mandibular tray.

17. The oral appliance of claim 16, wherein each of said engagement devices comprises a post and a cap, said cap is connected to a free end of said post, the opposite end of the post is connected to a respective one of said trays, and one edge of the cap is a declining portion that extends over a side of the post and toward said tray for retaining said elastic;
said declining portion of said first engagement device is disposed toward the posterior of said maxillary tray;
said declining portion of said second engagement device is disposed toward the anterior of the maxillary tray; and
said declining portion of said third engagement device is disposed toward the posterior of said mandibular tray.

18. The oral appliance of claim 12, wherein both said anterior face of said maxillary bite pad and said posterior face of said mandibular bite pad define guide planes disposed at an upward and forward slant.

19. In an oral appliance suited for treating snoring, sleep apnea, and sleep bruxism in a patient in need of treatment therefor, formed of a maxillary tray and a mandibular tray, said maxillary tray carrying a maxillary bite pad projecting downwardly toward an opposed mandibular occlusal surface of said mandibular tray, and the mandibular tray carrying a mandibular bite pad projecting upwardly toward an opposed maxillary occlusal surface of the maxillary tray, wherein the said maxillary bite pad is posterior to said mandibular bite pad such that upon sufficient relative posterior movement of the mandibular tray, the maxillary bite pad engages the mandibular bite pad and limits posterior movement of the mandibular tray, the improvement comprising:
said maxillary tray and mandibular tray are fitted, in use, to the respective maxillary and mandibular teeth of the patient with sufficient retention to be useful in positioning the patient's jaw; and
a smooth pad disposed over the occlusal surface of at least one of said trays, guarding said occlusal surface from engagement with the opposed bite pad.

20. The oral appliance of claim 19 wherein:
said at least one smooth pad comprises a maxillary smooth pad disposed anterior to said maxillary bite pad and covering said maxillary occlusal surface opposed to said mandibular bite pad, guarding the maxillary occlusal surface from engagement with the mandibular bite pad.

21. The oral appliance of claim 20, wherein said maxillary smooth pad and said maxillary bite pad are formed as a unitary structure.

22. The oral appliance of claim 19, further comprising:
a first engagement device carried on the outer side of said maxillary tray in proximity to the anterior end of said maxillary bite pad;
a second engagement device carried on the outer side of the maxillary tray, anterior to said first engagement device;
a third engagement device carried on the outer side of said mandibular tray in proximity to the posterior end of said mandibular tray; and
an elastic engaging the first and third engagement devices and extending around said second engagement device, whereby the elastic applies a force urging forward the mandibular tray.

23. The oral appliance of claim 22, wherein each of said engagement devices comprises a post and a cap, said cap is connected to a free end of said post, the opposite end of the post is connected to a respective one of said trays, and one edge of the cap is a declining portion that extends over a side of the post and toward said tray for retaining said elastic;
said declining portion of said first engagement device is disposed toward the posterior of said maxillary tray;
said declining portion of said second engagement device is disposed toward the anterior of the maxillary tray; and
said declining portion of said third engagement device is disposed toward the posterior of said mandibular tray.

24. The oral appliance of claim 19, wherein:
said at least one smooth pad comprises a mandibular smooth pad disposed posterior to said mandibular bite pad and covering said mandibular occlusal surface opposed to said maxillary bite pad, guarding the mandibular occlusal surface from engagement with the maxillary bite pad.

25. The oral appliance of claim 24, wherein said mandibular smooth pad and said mandibular bite pad are formed as a unitary structure.

* * * * *